(12) United States Patent
Maucec et al.

(10) Patent No.: US 8,920,029 B2
(45) Date of Patent: Dec. 30, 2014

(54) SAMPLE CONTAINMENT APPARATUS, SYSTEMS, AND METHODS

(75) Inventors: Marko Maucec, Englewood, CO (US); Ronald G. Dusterhoft, Katy, TX (US); Ronald A. Gibson, Duncan, OK (US); Richard D. Rickman, Duncan, OK (US)

(73) Assignee: Landmark Graphics Corporation, Houston, TX (US)

( * ) Notice: Subject to any disclaimer, the term of this patent is extended or adjusted under 35 U.S.C. 154(b) by 0 days.

(21) Appl. No.: 14/000,570

(22) PCT Filed: Dec. 12, 2011

(86) PCT No.: PCT/US2011/064445
§ 371 (c)(1),
(2), (4) Date: Sep. 27, 2013

(87) PCT Pub. No.: WO2012/121768
PCT Pub. Date: Sep. 13, 2012

(65) Prior Publication Data
US 2014/0021345 A1    Jan. 23, 2014

Related U.S. Application Data

(63) Continuation-in-part of application No. 13/040,396, filed on Mar. 4, 2011, now Pat. No. 8,507,868.

(51) Int. Cl.
| | |
|---|---|
| *H05G 1/00* | (2006.01) |
| *G01N 15/08* | (2006.01) |
| *G01N 23/04* | (2006.01) |
| *G01V 5/08* | (2006.01) |
| *G01N 33/24* | (2006.01) |

(52) U.S. Cl.
CPC .............. *G01V 5/085* (2013.01); *G01N 23/046* (2013.01); *G01N 15/082* (2013.01); *G01N 15/0806* (2013.01); *G01N 33/24* (2013.01)
USPC ............................................... 378/208; 73/38

(58) Field of Classification Search
CPC ..................... B01D 2321/185; B01D 2315/06; B01D 65/02

USPC ............................................... 73/38; 378/208
See application file for complete search history.

(56) References Cited

U.S. PATENT DOCUMENTS

| | | | |
|---|---|---|---|
| 4,649,737 | A | 3/1987 | Jones |
| 4,669,299 | A | 6/1987 | Closmann |

(Continued)

FOREIGN PATENT DOCUMENTS

| | | |
|---|---|---|
| GB | 2127559 A | 4/1984 |
| WO | WO-2012121768 A2 | 9/2012 |
| WO | WO-2012121768 A3 | 9/2012 |

OTHER PUBLICATIONS

"International Application Serial No. PCT/US2011/064445, International Preliminary Report on Patentability mailed May 3, 2013", 8 pgs.

(Continued)

*Primary Examiner* — Mark R Gaworecki
*Assistant Examiner* — Kenneth J Malkowski
(74) *Attorney, Agent, or Firm* — Schwegman Lundberg & Woessner, P.A.; Jennifer Trillsch

(57) ABSTRACT

Apparatus and systems may operate to enable positron emission imaging with a unitary chamber body having an open end that defines a hollow interior portion shaped to completely contain a flexible sleeve that is used to cover a core sample when the sleeve is seated within the hollow interior portion. An end cap may be formed to engage the open end of the chamber body, which is configured to attenuate gamma rays approximately eight times less than stainless steel, while supporting a pressure differential of at least 3 MPa between the chamber inlet and the outlet when fluid carrying a radioactive tag to generate the gamma rays flows through the hollow interior portion and the core sample via the inlet and the outlet. Additional apparatus, systems, and methods are disclosed.

20 Claims, 4 Drawing Sheets

(56) References Cited

U.S. PATENT DOCUMENTS

| | | | |
|---|---|---|---|
| 4,710,948 A * | 12/1987 | Withjack | 378/208 |
| 4,996,872 A | 3/1991 | Mueller et al. | |
| 5,065,421 A | 11/1991 | Morineau et al. | |
| 5,263,360 A | 11/1993 | Blauch et al. | |
| 5,297,420 A | 3/1994 | Gilliland et al. | |
| 5,493,226 A | 2/1996 | Honarpour et al. | |
| 5,783,760 A | 7/1998 | Haines et al. | |
| 6,401,523 B1 | 6/2002 | Fernandes et al. | |
| 6,517,774 B1 | 2/2003 | Bray et al. | |
| 8,507,868 B2 | 8/2013 | Maucec | |
| 2006/0253013 A1 | 11/2006 | Cable et al. | |

OTHER PUBLICATIONS

"International Application Serial No. PCT/US2011/064445, Search Report mailed Apr. 10, 2012", 2 pgs.

"International Application Serial No. PCT/US2011/064445, Written Opinion mailed Apr. 10, 2012", 5 pgs.

"Australian Application Serial No. 2011361714, Examination Report mailed Apr. 30, 2014", 4 pgs.

"Fiberspar FS LPJ 4" 1500(E)", Product Data Sheet, Rev. 1.0, (Mar. 31, 2010), 1 pg.

Brewer, R., "Criticality Calculations with MCNP5™: A Primer", LA-UR-09-00380, Los Alamos National Laboratory, World Wide Web Release, (Jan. 2009), 202 pgs.

Buffler, A., et al., "PEPT Cape Town: A new positron emission particle tracking facility at iThemba LABS", *Proceedings of International Topical Meeting on Nuclear Research Applications and Utilization of Accelerators. IAEA International Topical Meeting on Nuclear Research Application and Utilization of Accelerators*, Vienna, (2010), 1-8.

De Graaf, B. M., "Determining the Effect of Shielding for an Eye Exposed to Secondary Particles Produced by Galactic Cosmic Rays using MCNPX Modeling", Master of Science Thesis, University of Cincinnati, (Oct. 2010), 40 pgs.

Foster, B. E., et al., "X-ray Mass Attenuation Coefficients in the Range of 50 to 150 kvp With Data for Several Reactor Materials", Oak Ridge National Laboratory Report, ORNL-3552, (Feb. 1964), 53 pgs.

Hubbell, J. H., et al., "Tables of X-Ray Mass Attenuation Coefficients and Mass Energy-Absorption Coefficients from 1 keV to 20 MeV for Elements Z=1 to 92 and 48 Additional Substances of Domestic Interest", (Abstract), [online]. Retrieved from the Internet: <URL: http://www.nist.gov/pml/data/xraycoef/index.cfm>, (2009), 1 pg.

McGregor, D. S., et al., "Thermal neutron detection with cadmium$_{1-x}$ zinc$_x$ telluride semiconductor detectors", *Nuclear Instruments and Methods in Physics Research A*, 381 (1996), 498-501.

Yu, H., et al., "Accuracy and borehole influences in pulsed neutron gamma density logging while drilling", *Applied Radiation and Isotopes*, 69, (2011), 1313-1317.

"Mexican Application Serial No. MX/a/2013/010018, Office Action mailed May 5, 2014".

"European Application Serial No. 11860180.6, Extended European Search Report mailed Jul. 31, 2014", 15 pgs.

Ogilvie, S. R. et al., "The influence of deformation bands upon fluid flow using profile permeametry and positron emission tomography", *Geophysical Research Letters*, vol. 28, No. 1, (2001), 61-64

* cited by examiner

SAMPLE CONTAINMENT APPARATUS, SYSTEMS, AND METHODS

RELATED APPLICATION

This application is a U.S. National Stage Filing under 35 U.S.C. 371 from International Application No. PCT/US2011/064445, filed on 12 Dec. 2011, and published as WO 2012/121768 A2 on 13 Sep. 2012; which international application is a continuation-in-part of prior U.S. patent application Ser. No. 13/040,396, filed Mar. 4, 2011 and claims priority benefit to U.S. patent application Ser. No. 13/040,396, filed Mar. 4, 2011, which applications and publication are incorporated herein by reference in their entirety.

BACKGROUND

Positron emission particle tracking (PEPT) can be used to create images of fluid movement through geological formation core samples by tracking the location of a radioactive tag that moves through the sample with the fluid. To track and image dynamic fluid front movement, it has been experimentally determined that using a radioactive tag and an exposure of about 50 microCi is sufficient to provide a useful signal-to-noise ratio when a positron emission tomography (PET) camera is used.

This amount of exposure, which might be considered to be the lower limit of detection, corresponds to approximately $2 \times 10^6$ detected events per second, and assumes there is no attenuation of the radiation provided by the tag.

In a practical imaging system, the attenuation of gamma-rays between source and detector is of course not zero. Indeed, system attenuation can amount to several orders of magnitude, as gamma-rays interact with the inspected core sample, surrounding instrumentation, and the detector itself. In practical terms, this indicates a useful level of activity for the radioactive tracer tag in the core sample to be on the order of mCi.

Unfortunately, when stainless steel containers that are typically used to transport core samples are also used in imaging analysis, the number of events is attenuated even further, reducing the number of detected tag generation events to less than $2 \times 10^5$ per second. This amount of attenuation, which is about ten times what occurs in a non-attenuating environment, prevents useful imaging or tracking of the tagged fluid.

DETAILED DESCRIPTION

Figure 1:
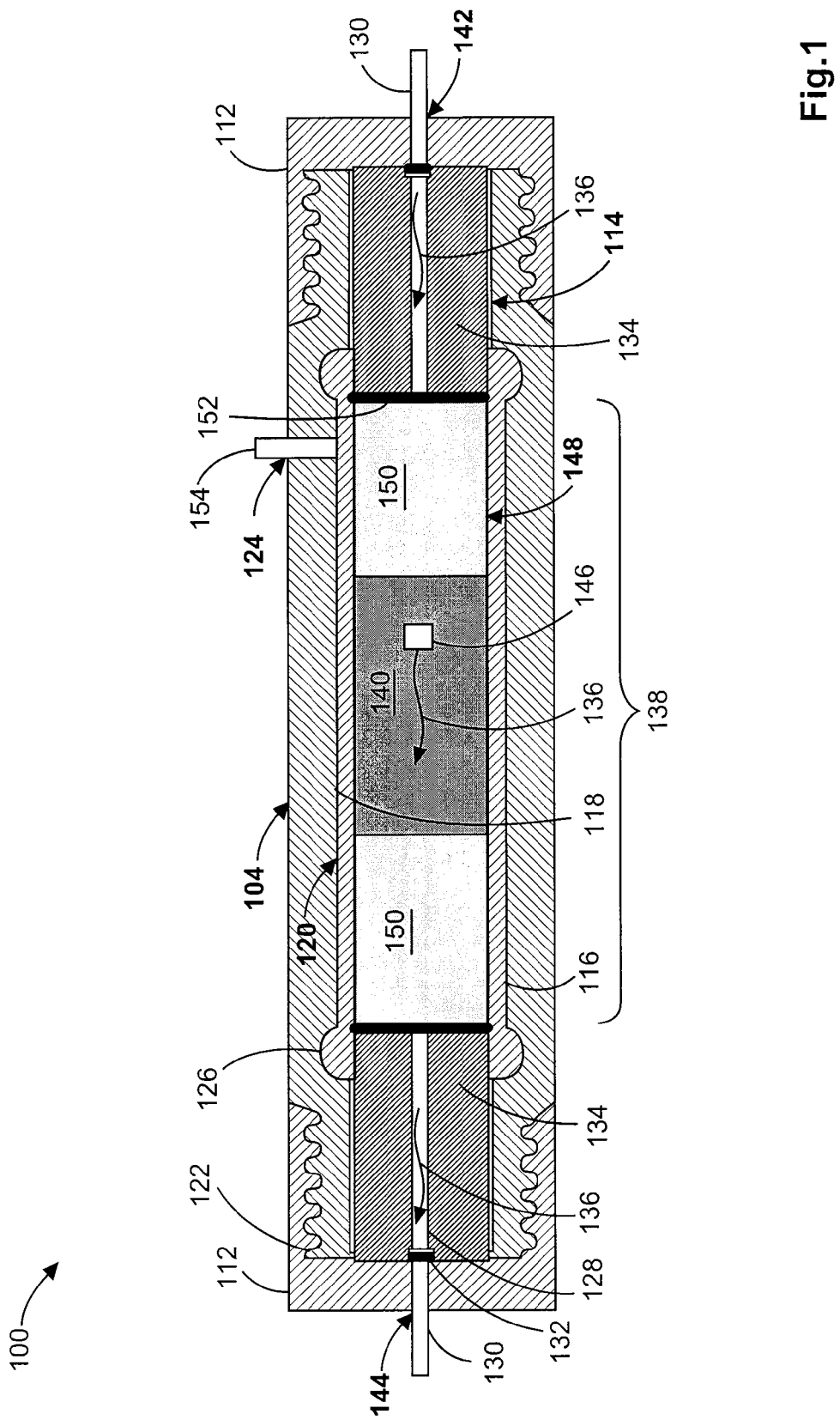
FIG. 1 is a block diagram of an apparatus according to various embodiments of the invention.

PEPT is basically a technique for measuring the trajectory of one or more tags, which may be used to tag a solid rock particle or a fluid. The tag may be any radioactive nuclide (radionuclide) capable of positron emission. In FIG. 1, for example, the trajectory of a single rock particle tagged with a radio nuclide tag is illustrated using PEPT and a PET camera. The radionuclide tag decays through the emission of a positron, which is the antiparticle of an electron. A positron produced in a nuclear decay will rapidly annihilate with an electron, resulting in a pair of 511 keY gamma rays that are emitted almost in opposite directions. If both of these gamma rays are detected at two different points, thereby defining a line of response ("LOR"), then the origin of the gamma ray emissions must have occurred somewhere along the LOR. In other words, the LOR substantially corresponds to a line joining a pair of opposing detectors.

The position of the radionuclide tag can be determined within the field of view of a PET camera using only a small number of measured LOR's.

The activity of the tag, however, must be sufficient for enough LOR's to be measured in order to accurately reflect the trajectory of the moving tag. In particular, tags of significantly smaller sizes must be used for PEPT to be reliably accurate for determining fluid mobility in small-scale shale pores. In principle, only two detectors are necessary, however, additional detectors may be used as long as they are paired—meaning positioned opposite one another along a line passing through the center of the PET camera. Because many thousands of gamma-ray emissions can be detected with a PET camera and processed each second, the possibility of determining the position of one or more fast moving radionuclide tags may be realized. Consequently, PEPT may be used to determine fluid mobility in rock samples by tagging a fluid with one or more radionuclide tags.

Many embodiments may be implemented through a computer-executable program of instructions, such as program modules, generally referred to as software applications or application programs executed by a computer. The software may include, for example, routines, programs, objects, components, and data structures that perform particular tasks or implement particular abstract data types. The software forms an interface to allow a computer to react according to a source of input. The software may also cooperate with other code segments to initiate a variety of tasks in response to data received in conjunction with the source of the received data. The software may be stored and/or carried on any variety of memory media such as CD-ROM, magnetic disk, bubble memory and semiconductor memory (e.g., various types of RAM or ROM). Furthermore, the software and its results may be transmitted over a variety of carrier media such as optical fiber, metallic wire and/or through any of a variety of networks such as the Internet.

Moreover, those of ordinary in the art will appreciate that embodiments of the invention may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present invention. The invention may be practiced in distributed-computing environments where tasks are performed by remote processing devices that are linked through a communications network. In a distributed computing environment, program modules may be located in both local and remote computer storage media including memory storage devices. Embodiments of the invention may therefore, be implemented in connection with various hardware, software and combinations thereof, in a computer system or other processing system.

Some embodiments are realized using a system for implementing the invention on a computer. The system includes a computing unit, sometimes referred to a computing system, which contains memory, application programs, a client interface, a video interface, a processing unit and a PET camera. The computing unit is only one example of a suitable computing environment and is not intended to suggest any limitation as to the scope of use or functionality of the invention.

The PET camera may include any conventional PET camera, such as, for example, the ECAT 'EXACT' 3D model 966 PET camera manufactured by Siemens. The camera has 48 standard bismuth germanate detector elements grouped in blocks of 8×8 forming a detector ring with a diameter of 82 cm and an axial field of view of 23.4 cm. The camera is useful due to its size. The camera is capable of maintaining a sustained data acquisition rate of about 4 million coincidence events per second. The camera also has a useful geometry for studying cylindrical systems in three dimensions and would allow handling of large rock samples, which represents a tremendous improvement over the standard petrophysical core-plug measurements in rock physics labs.

A shale rock sample about 50 cm in height and about 20 cm in thickness may be positioned in a pressurized container. The container is pressurized to simulate pressures and/or temperatures imposed on the rock sample in-situ. Detectors detect emissions generated by pairs of registered incident gamma rays, which are combined in coincidence circuitry within a short time window. In this manner, position information is gained from the detected radiation without the need of a physical collimator (i.e. electronic collimation). For simplicity, the PET camera is described in relation to a pair of detectors. In practice, all of the detectors in the detector ring are directly wired to the Data Acquisition Module. Alternatively, all of the detectors in the detector ring may be wirelessly connected to the Data Acquisition Module.

Alternatively, the PET camera could be manufactured on a much smaller scale and positioned in a drill string for deployment downhole in a wellbore. Existing technology, such as the Halliburton RSCT and HRSCT coring tools, could be retrofitted to host a smaller scale PET camera. For example, the RSCT tool drills perpendicularly to the bore-hole to recover rock samples of 15/16" in OD and 1¾" in length. Each rock sample may be withdrawn into a container in the tool that can be pressurized for delivery of the fluid tagged with the radionuclide tag. Depending on the environmental conditions downhole, the PET camera and the computing unit (except the client interface/video interface) may be carried by the drill string with the RSCT tool. Alternatively, only the PET camera may be carried by the drill string with the RSCT tool if the environmental conditions are not conducive to positioning the computing unit in the drillstring. Fluid mobility data can be transmitted to the client interface/video interface at the surface for analysis over a fast optical line, for example. After determining fluid mobility for the rock sample, it may be transferred to a storage tube.

The memory primarily stores the application programs, which may also be described as program modules containing computer-executable instructions, executed by the computing unit for implementing various embodiments. The memory may include a Data Acquisition Module and a Time-Lapse Data Analysis and Interpretation Module, to enable some of the methods illustrated and described.

The Data Acquisition Module records raw data (gamma ray emissions) in a list mode file. The gamma ray emissions are recorded as detected signals, which are recorded in chronological order so that each signal has a time stamp and the coordinates for each detector.

When the signals significantly match or overlap for a pair of opposing detectors, a coincident event is defined. This mode of recording the raw data is for recording coincidence events and is routinely utilized with a PET camera. Channels 1 and 2, for example, illustrate two independent signals representing a pair of opposing gamma ray emissions detected by a pair of opposing PET camera detectors at different times. The sum channel separates the coincidence events from other events (signals) by summing to determine a coincidence event within a predetermined short time interval. The Data Acquisition Module may therefore, be calibrated in a way to amplify the signal for only the time intervals where the amplitudes of the signals for channels 1 and 2 substantially overlap within a certain predefined short time interval. The coincidence event for the amplified signal amplitude therefore, may correspond to a pair of opposing gamma rays detected coincidentally within the predefined time interval. Each coincident event is recorded in chronological order so that each coincidence event has a time stamp and the coordinates for each of the two opposing detectors. Based on the coordinates for each of the two opposing detectors, the LOR may be easily determined. The Data Acquisition Module may record thousands of coincidence events per second. The list mode file therefore, secures the highest amount of available information for the raw data. Although case dependent, the size of the list mode file is much larger than that of a sinogram and can exceed hundreds of megabytes or even gigabytes of data. Once recorded, the data in the list mode file must be converted to form images that can then be used to determine fluid mobility.

The Time-lapse Data Analysis and Interpretation Module converts the data in the list mode file to images that can be used to determine fluid mobility. The conversion may be performed using conventional methods such as, for example, simple backprojection, filtered backprojection, or iterative methods. The Time-Lapse Data Analysis and Interpretation Module uses a different method, however, to convert the list mode file to images. Each list mode file is segmented into time slices (typically of the order of a millisecond). The time-sliced data are triangulated to get the x,y,z,t coordinates for each tag, which enables tracking multiple tags in the field of view of the PET camera simultaneously. In this manner, tracking multiple tags may be extended to images and optimized for the size of the data matrices related to the number of image voxels. Any, well known and widely available image processing tool may be applied to optimize the quality of the image. Optionally, attenuation correction may be applied to improve the resolution of the processed voxel image by correcting for the so-called scattered and random coincidence, which contributes to the uncertainty of interpretation. Furthermore, uncertainty is associated with the speed of the moving tag. It seems that for slowly moving or stationary tags, the uncertainty is about half the detector size (i.e. about 2 mm). As the speed of the tag increases, this uncertainty increases proportionally and may require further investigation. Dealing with "noncontinuous" data (i.e. fluid/gas propagation discretized into (ultra) short timeframes) may reduce this uncertainty, however.

Although the computing unit is shown as having a generalized memory, the computing unit typically includes a variety of computer readable media. By way of example, and not limitation, computer readable media may comprise computer storage media. The computing system memory may include computer storage media in the form of volatile and/or nonvolatile memory such as a read only memory (ROM) and random access memory (RAM).

A basic input/output system (BIOS), containing the basic routines that help to transfer information between elements within the computing unit, such as during start-up, is typically stored in ROM. The RAM typically contains data and/or program modules that are immediately accessible to and/or presently being operated on by the processing unit. By way of example, and not limitation, the computing unit includes an operating system, application programs, other program modules, and program data.

The components shown in the memory may also be included in other removable/nonremovable, volatile/nonvolatile computer storage media or they may be implemented in the computing unit through application program interface ("API"), which may reside on a separate computing unit connected through a computer system or network. For example only, a hard disk drive may read from or write to non-removable, nonvolatile magnetic media, a magnetic disk drive may read from or write to a removable, non-volatile magnetic disk, and an optical disk drive may read from or write to a removable, nonvolatile optical disk such as a CD ROM or other optical media. Other removable/non-removable, volatile/non-volatile computer storage media that can be used in the exemplary operating environment may include, but are not limited to, magnetic tape cassettes, flash memory cards, digital versatile disks, digital video tape, solid state RAM, solid state ROM, and the like. The drives and their associated computer storage media discussed above provide storage of computer readable instructions, data structures, program modules and other data for the computing unit.

A client may enter commands and information into the computing unit through the client interface, which may be input devices such as a keyboard and pointing device, commonly referred to as a mouse, trackball or touch pad. Input devices may include a microphone, joystick, satellite dish, scanner, or the like. These and other input devices are often connected to the processing unit through a system bus, but may be connected by other interface and bus structures, such as a parallel port or a universal serial bus (USB).

A monitor or other type of display device may be connected to the system bus via an interface, such as a video interface. A graphical user interface ("GUI") may also be used with the video interface to receive instructions from the client interface and transmit instructions to the processing unit. In addition to the monitor, computers may also include other peripheral output devices such as speakers and printer, which may be connected through an output peripheral interface.

Although many other internal components of the computing unit are not shown, those of ordinary skill in the art will appreciate that such components and their interconnection are well known. A method embodiment will now be described.

Initially, a porous rock sample is selected. The rock sample may be selected based upon a number of criteria including, but not limited to, porosity characteristics and permeability. Shale, for example, may be selected as a porous rock sample with a permeability of less than one micro-darcy.

Then a fluid for the rock sample is selected. The fluid may be selected, for example, based upon various criteria including, but not limited to, fluid indigenous to the rock sample. Thus, the fluid may be a gas or a liquid. If a shale rock sample is selected, then a fluid for the rock sample representing an indigenous fluid may be methane ($CH_4$) gas since methane is the main chemical constituent in shale gas.

Then a tag for the fluid is selected. The radionuclide tag should resemble the fluid it is being used to tag for consistent results in determining fluid mobility. For example, a liquid should be tagged with a liquid radionuclide tag and a gas should be tagged with a gas radionuclide tag. For even better results, the radionuclide tag should have a chemical composition as close to the chemical composition of the fluid as possible. In this manner, the mobility of the fluid tag with the radionuclide tag will be closer to the true mobility of the fluid in the rock sample without the radionuclide tag. In turn, the activity of the radionuclide tag depends on both its size and composition. Thus, for shale, if a methane ($CH_4$) gas is selected as the fluid, a useful radionuclide tag for the gas would be $C_{11}$.

Then the rock sample is placed in a pressurized container. The pressurized container, for example, may resemble the pressurized container described previously.

Then the fluid and the tag are introduced into pores within the rock sample. The fluid and the tag may be introduced into the pores within the rock sample by injecting the fluid and the tag into the pressurized container at one end under a constant pressure and a constant temperature. Alternatively, the fluid and the tag may introduced into the pores within the rock sample by injecting the fluid and the tag directly into the pores within the rock sample before the rock sample is placed in the pressurized container and applying a constant pressure and a constant temperature to the rock sample after it is placed in the pressurized container with the fluid and the tag. The fluid is tagged when it is introduced with the tag into the pores within the rock sample. At this point, the tag attaches to the fluid as it traverses with the fluid through the pores within the rock sample and/or the tag travels with the fluid as it traverses with the fluid through the pores within the rock sample. Furthermore, multiple tags may be introduced with the fluid into the pores within the rock sample. The fluid and the tag are introduced into the pores within the rock sample at a constant flow rate, a constant pressure and a constant temperature. The flow rate, the constant pressure, the constant temperature, the fluid and the tag may be selected based upon a flow rate, a pressure, and a temperature for a fluid that is indigenous to the rock sample, which represents a target fluid.

Then, gamma-ray emissions from the tag are recorded as the tag traverses with the fluid through the pores in the rock sample. The gamma-ray emissions may be recorded in a list mode file. The gamma-ray emissions may be recorded using the PET camera and the Data Acquisition Module described previously.

Then the gamma-ray emissions recorded in previously are converted into images. The gamma-ray emissions may be converted into images at a rate of more than one image every second using the Time-Lapse Data Analysis and Interpolation module described previously.

Next the images are displayed. The images may be displayed next to each other or consecutively using the client/video interface previously described. Fluid mobility may therefore, be determined by viewing the displayed images or using the displayed images to determine a permeability for the rock sample.

The proposed time-lapse PEPT technology therefore, greatly improves over state of the art imaging technology because it actually images the fluid propagating through the rock sample under different net pressures. The time-lapse PEPT goes even further by performing uncompromised high-resolution imaging of fluid mobility and interactive scanning of rock samples with small-scale pores unprecedented in the rock physics industry.

Horizontal drilling and hydraulic fracturing have made it feasible to extract huge amounts of natural gas trapped in shale formations. The objective of fracturing techniques is to expose the maximum possible surface area of the rock formation and provide a reasonable path for the fluid to produce back to the wellbore. Fracturing techniques are therefore, designed to achieve long effective fracture half-lengths and improve fracture conductivity in rocks with milli-darcy (mD) to micro-darcy ($\mu$D) rock permeabilities.

Fracturing techniques however, should also address nanodarcy (nD) rock permeabilities in shale rocks that geologists used to consider seals. Permeability of a rock sample is defined as the ability of the rock sample to transmit fluids through the pore spaces, which influences the fluid flow rate, the fluid's movement and drainage of the fluid. The experimental determination of permeability in shale rock samples by standard rock physics laboratory measurements is extremely challenging and time-consuming. Therefore, rather than determining the bulk permeability for the shale rock sample, it is common practice to determine the Fracture Conductivity Ratio ($C_r$) by the following equation:

$$C_r = (k_{fracture} \cdot W_{fracture})/(k_{reservoir} \cdot l_{fracture})$$

where $k_{fracture}$ refers to fracture permeability (in mD), $W_{fracture}$ represents the width of the fracture (in ft), $k_{reservoir}$ is the formation/reservoir permeability (in mD) and $l_{fracture}$ represents the fracture half-length (in ft). It is common to refer to the product of $k_{fracture}$ and $W_{fracture}$ as the fracture conductivity (in mD ft).

The quantitative information on the fluid mobility, acquired with the time-lapse PEPT imaging will directly enhance the knowledge of k reservoir, W fracture and l fracture parameters. As such, the time-lapse PEPT imaging will provide a unique quantitative estimate on how the fluid mobility changes as a result of fracturing, particularly at high fluid injection rates, where the conventional PET imaging fails. Furthermore, the time-lapse PEPT imaging will reduce the uncertainty in quantifying the Fracture Conductivity Ration (Cr) and moreover, the Natural Fracture Conductivity Index (NFCI) by direct one-to-one comparison of the fluid mobility of the pre-fracture rock sample with the post-fracture rock sample. This will provide for more accurate determination of fracturing production success, through the estimation of the Stimulated Reservoir Volume (SRV), defined as the product of the Stimulated Area and the Net Pay. The standard industrial practice for calculating SRV's usually introduces high uncertainty and systematic error in the volume estimates, mainly due to the inaccurate and uncertain estimates of the fracture connectivity. The three-dimensional PEPT fluid propagation imaging will produce a) more accurate estimates on the directionality of fractures deduced from the fluid distribution as a function of time, b) more quantitatively sound estimates of fracture connectivity and c) improved correlation and reduced error in the estimates of SRV.

Recent laboratory experiments performed on a number of shale rock samples reveal that the effective permeability of the shale rock sample can be changed from nD to µD when the shale rock sample is fractured. This suggests that even unsupported fractures (i.e. without the permeability support by proppant packs) may be capable of contributing to production in ultra-low permeability shale rocks. It is foreseen that by using the time-lapse PEPT imaging, it will be possible to derive quantitative (at least empirical) estimates on the correlation between the effective permeability of fractured rock, the estimates of SRV and the speed of fluid propagation front, directly from the reconstructed three-dimensional PEPT image. This will enable optimization and more time- and cost-efficient design of the fracturing and refracturing jobs by improving the knowledge on the correlation of fluid propagation and the fracturing attributes (e.g. closure stress), stimulation parameters (e.g. presence and type of proppants) and production data (e.g. pressure) as well as reduce uncertainty of the practical operational and economic variables, such as, for example: a) the amount of extractable hydrocarbons (e.g. Original Gas In Place), b) optimum well perforation interval, c) drainage area/volume of wells, d) recovery factor, e) optimum spacing units and f) optimum steer, direction and angle of the wells.

In order to perform PEPT experiments with shale-gas core samples under realistic fracturing conditions, improving knowledge of the correlation of fluid propagation and the fracturing attributes, stimulation parameters, and production data under various pressure-closure stresses, the core sample in question should be encapsulated in a container that maintains the integrity of the core sample and facilitates the supply of fluids in the sample under a variety of pressures. Standard containers, such as the Hassler Sleeve Device (HSD), are constructed out of solid stainless steel, which acts as strong attenuator of gamma-rays with energies below 1 MeV. Thus, the HSD is not useful for PET imaging of core samples.

To address some of the challenges described above, as well as others, apparatus, systems, and methods for low-attenuation containment of core samples and radioactive tags are described. These solutions include the discovery that certain thermoplastic materials can be used to make a container for core samples that enables the penetration of sufficient radiation for PET imaging, while supporting a pressure differential across the container that approximates down hole conditions. Unlike stainless steel, these materials are relatively low in cost, and the resulting container is easy to manufacture.

Using these materials and the container construction described herein, stochastic (Monte Carlo) modeling simulations of radiation transport indicate that attenuation with respect to stainless steel is reduced by a factor of approximately eight times, which means that a tagged fluid event activity of only 6000 mCi is needed to achieve useful counting statistics. This corresponds to the tag in the fluid generating approximately $2 \times 10^{11}$ events/second. As a matter of contrast, successful PET imaging using a stainless steel container would dictate using a source that generates about $5 \times 10^4$ mCi (where 1 mCi=1000 microCi) of activity. Thus, using the novel apparatus, systems, and methods described herein, tags of much lower activity can be used to create useful images.

In addition, statisticians of ordinary skill realize that reducing the standard deviation (or the dissipation around the mean value) directly corresponds to improving the precision of measurement. Thus, for the same experimental setup, reducing gamma ray attenuation in this case by a factor of approximately eight times means the data acquisition integration time can also be reduced by a factor of approximately eight. In terms of counting statistics, the standard deviation of the count rate can thus be reduced by a factor of approximately three times, which improves the measurement precision by the same amount.

The thermoplastic materials described herein have been used to construct a container for core samples that will sustain a minimum imposed pressure of 10 MPa. This container can be used to replace the HSD in a variety of instances, since it is sufficiently strong, uses less costly materials, and is easier to manufacture.

In some embodiments, various container embodiments are constructed using the amorphous polymer polyetherimide (PEI). Although the mechanical properties of PEI are well known to those of ordinary skill in the art (e.g., it has a tensile strength of about 115 MPa), this material has never been successfully formed into a reusable core sample container with sufficient strength to sustain the stresses imposed by realistic down hole conditions. However, destructive testing has confirmed that a PEI container, constructed as described herein, can indeed provide the imaging capability noted, while realistic down hole pressure conditions are imposed. The details of this construction will now be described.

FIG. 1 is a block diagram of an apparatus 100 according to various embodiments of the invention. The apparatus 100 may be constructed in a number of different ways.

For example, an apparatus 100 may comprise a unitary chamber body 104 with a pressure-coupling port 124, end plugs 134, and one or more end caps 112. The hollow interior portion 114 of the chamber body 104 has an inner diameter 116 that is substantially the same as the outer diameter 118 of the central portion 138 of a flexible sleeve 120 (e.g., a unitary sleeve made of rubber) that is seated within the body 104. For the purposes of this document, the term "unitary" is applied to an item (e.g., the unitary chamber or the unitary sleeve) when the item is formed from a single piece of material.

The engaging end(s) 122 of the chamber body 104 may use threads for engagement with the end cap(s) 112. Among other ways to engage the end caps 112 with the chamber body 104, threads are efficient. For example, threaded end caps 112 can easily be used to apply a compressive preload on the core sample 140 disposed inside the sleeve 120. Unlike the HSD and other containers used to transport core samples 140, the ends 126 of the sleeve 120 are completely encapsulated within the chamber body 104.

Orifices 128 exist in the end plugs 134, which may be combined in operation with o-rings 132 to accept and seal lengths of inlet and outlet tubing 130. Thus, the end plugs 134 sealingly engage the tubing 130.

The inlet 142 and the outlet 144 of the apparatus 100 may be formed in the end caps 112. When sufficient pressure is applied, fluid 136 (e.g., formation fluid) can flow from the inlet 142 to the outlet 144 of the chamber body 104 via the tubing 130. The inlet 142 and outlet 144 may be formed so as to allow the tubing 130 to pass through them, but not necessarily so as to seal to the tubing 130 against external pressure.

In some embodiments, there may be an annular space between the outside of the sleeve 120 and the inside of the chamber body 104 (such as when the diameters 116, 118 form an annulus between them). The port 124 formed into the side of the chamber body 104 allows fluid 136 to be pumped into this annulus, compressing the sleeve 120 around the core sample 140 disposed within the sleeve 120.

In most embodiments, the core sample 140 is not radioactive. Rather, a radioactive tag 146 is inserted into the fluid 136, and the progress of the fluid 136 as it moves through the core sample 140 is monitored by monitoring the travel path of the tag 146. Under sufficient pressure, the fluid 136, as well as the tag 146, are forced through the pore space of the core sample 140.

A minimum differential pressure (the pressure difference between the inlet 142 and the outlet 144) across the core sample 140 of approximately 3.5 MPa can be used to initiate flow of the fluid 136. To avoid having the fluid 136 flow in the core sample 140 and the sleeve 120, approximately 7 Mpa of fluid pressure is applied to the port 124.

A variety of materials can be used to form different parts of the apparatus 100. For example, the chamber body 104, the end caps 112, and the end plugs 134 can all be made from Ultem® 1000 PEI. The tubing 130 that serves the inlet 142 and outlet 144, as well as the tubing 154 that serves the port 124 may have an outside diameter of approximately 3 mm, and may be made of polyetheretherketone (PEEK) plastic or stainless steel. The tubing 130, 154 may be rated at a working pressure of approximately 35 MPa.

Spacing and support for the core sample 140 can be provided by the spacers 150, if desired. For example, spacers 150 can be useful when split core samples 140 are used, to give each piece of the core sample 140 additional support.

The spacers 150 are used to center the core sample 140 within the chamber body 104, and to support the sleeve 120 when pressure is applied to the annulus around the outside of the sleeve 120. The spacers 150 may be formed from a plastic, such as Ultem® material, or a particulate, such as sand.

If sand is used to form the spacers 150, the sand may comprise sieved, graded, and round particles. A bonding agent can be used in conjunction with the sand to form a single piece, high permeability spacer 150 as a supporting mechanism. The pore size in the spacers 150 is usually greater than the pore size in the sample 140, so as not to restrict the flow of the fluid 136 through the sample 140. A wire screen 152 can be disposed between the spacers 150 and the end plugs 134, with a mesh size sufficiently small to prevent the movement of particles that make up the spacers 150.

In some embodiments, the chamber body 104 and the end caps 112 are machined from approximately 50 mm diameter Ultem® 1000 material bar stock. The end plugs 134 may be machined from approximately 30 mm diameter Ultem® 1000 material bar stock. The spacers 150 may be machined from a variety of plastic materials.

To assemble the apparatus 100, the tubing 130 is inserted through the inlet 142 and outlet 144. O-rings 132 are applied over the ends of the tubing 130, which are flared to hold the tubing 130 in place via counter-bores in the end plugs 134 and the end caps 112 to form a seal.

High pressure metal fittings can be used on the other end of the tubing 130, 154 to connect to pumps, etc. The sleeve 120 is lubricated and folded over so that it can be inserted into the chamber body 104, with the ends of the sleeve 126 fitting into conformal depressions in the hollow interior portion 114 of the chamber body 104 when the sleeve 120 is seated within the body 104. At this point, the core sample 140 can be disposed within the sleeve 120. Spacers 150 may be inserted into the chamber body 104, after which the end plugs 134 are inserted into the hollow interior portion 114 chamber body 104, so as to fit into the ends 126 of the sleeve 120.

In many embodiments, the end plugs 134 are a relatively tight fit into the ends 126 of the sleeve 120. The plugs 134 serve to expand the bulbous ends 126 of the sleeve to form a fluid-tight seal against the wall that forms the hollow interior portion 114 of the chamber body 104, and the sides of the plugs 134 (e.g., where the screens 152 are shown in FIG. 1). The end caps 112 serve to prevent the plugs 134 from blowing out of the chamber body 104 when pressure is applied across the chamber body 104, from the inlet 142 to the outlet 144. Pressure can also be applied to the annular space between the sleeve 120 and the hollow interior portion 114 of the chamber body 104, via the port 124 and tubing 154, to improve the seal provided by the sleeve 120 against the core sample 140. This port pressure is generally on the order of twice the flow pressure, to help force the fluid 136 to flow through the sample 140, rather than around it.

The fluid 136 may comprise water, salt water, kerosene, or nitrogen gas, among others. Flow rates through the tubing 130 are generally low, but the flow capacity of the core sample 140 is typically much lower, so as to set the maximum flow rate (often less than 100 cc/minute) and/or differential pressure from the inlet 142 to the outlet 144. Thus, many embodiments may be realized.

For example, an apparatus 100 may comprise a unitary chamber body 104, end plugs 134, a port 124, and at least one engaging end cap 112. The unitary chamber body 104 has a first engaging end (e.g., near the inlet 142) and a hollow interior portion 114 shaped to accommodate a flexible sleeve 120 having a central portion 138 attached to exterior protruding end portions 126. Thus, when the flexible sleeve 120 is seated within the hollow interior portion 114 of the chamber body 104, the central portion 138 and the end portions 126 are entirely contained within the hollow interior portion 114 of the chamber body 104.

The end plugs 134 are shaped to fit within outer ends of the hollow interior portion 114 and an interior portion 148 of the flexible sleeve 120. Each of the end plugs 134 has an orifice 128 configured to enable fluid conduction along a path substantially parallel to a longitudinal axis of the chamber body 104, the path including the inlet 142 of the apparatus 100, each orifice 128, and an outlet 144 of the apparatus 100.

The port 124 is configured to pass through a wall of the chamber body 104 and to couple pressure imposed external to the chamber body 104 to the hollow interior portion 114 when the chamber body 104 is sealed against the pressure. The end cap(s) 112 are configured to engage the engaging end(s) 122 of the chamber body 104; the end cap(s) 112 can provide the inlet 142 and/or the outlet 144. Thus, the chamber body 104 may accommodate two end caps 112 (as shown in FIG. 1), each engaging ends of the chamber body 104. Engagement can be provided using threads in the end caps 112, to engage threaded portions 122 of the exterior portion of the chamber body 104.

The orifices 128 in the end plugs 134 can be approximately centered in the plugs 134. Thus, each orifice 128 may be substantially centered in its respective end plug 134.

Each end plug 134 may be long enough to span the distance from the end 122 of the chamber body, past one of the sleeve ends, and onward to just past one of the protruding end portions 126 of the sleeve 120, providing support for the end of the sleeve and preventing movement of the core sample 140 and core spacers 150 within the chamber body 104. Thus, one or more of the end plugs 134 may have a length approximately equal to the distance from an engaging end 122 of the chamber body 104, past one of the protruding end portions 126 attached to the central portion 138 of the flexible sleeve 120, when the sleeve 120 is seated within the hollow interior portion 114 of the chamber body 104.

The chamber body 104 may be formed in a variety of shapes, such as a rectangular block, or a cylinder. Thus, the chamber body 104 may be formed as a substantially hollow cylinder.

The end caps may be formed to match the exterior dimensions of the chamber body. For example, if the chamber body 104 is formed as a rectangular block, the width of the end caps may match the width of the outer wall of the block. If the chamber body is formed as a cylinder, the end caps may have an exterior diameter that matches the exterior diameter of the chamber body. Thus, an exterior dimension of the engaging end cap 112 may be formed to substantially match an exterior dimension of the chamber body 104, as shown in FIG. 1.

Core spacers 150 can be used to locate a core sample 140 within the chamber body 104. The core spacers may comprise plastic. Thus, the apparatus 100 may comprise a pair of core spacers 150 to substantially center a core sample 140 within the hollow interior portion 114 of the chamber body 104, between the end plugs 134.

The core spacers may be made of sand, perhaps adhesively bonded with a bonding agent. Screens can be used to prevent particles of the sand from exiting the chamber outlet under pressure. Thus, the apparatus 100 may comprise a pair of screens 152 disposed between the core spacers 150 and the end plugs 152, wherein the core spacers 150 comprise bonded sand.

Several components of the apparatus can be made of a high tensile strength thermoplastic. For example, the chamber body 104, the end plugs 134, and the end cap(s) 112 may comprise a thermoplastic having sufficient tensile strength to withstand a pressure differential of more than 3 MPa between the inlet and the outlet. This thermoplastic may comprise PEI, for example.

The port may be coupled to port pressure compensation tubing. Thus, the apparatus 100 may comprise port pressure compensation tubing 154 disposed within the port 124.

Flow tubing can be used to conduct the fluid to and from the chamber body. The flow tubing can be sealed to the chamber body using o-rings. Thus, the apparatus 100 may comprise flow tubing 130 configured to fit within at least one of the inlet 142 or the outlet 144. A pair of o-rings 132 may be disposed around the flow tubing 130 and within counter-bores in the end plugs 134 and the hollow interior portion 114 of the chamber body 104. Therefore, many additional embodiments may be realized.

For example, the chamber body 104 may be configured to reduce a corresponding standard deviation of the detected particle count rate by approximately three times. In this case, the apparatus 100 may comprise a unitary chamber body 104 having an open end defining a hollow interior portion 114 shaped to completely contain a flexible sleeve 120 when the sleeve is seated within the hollow interior portion, the sleeve to be used to cover a core sample 140. The apparatus 100 further comprises at least one end cap 112 formed to engage the open end of the chamber body 104 to support a pressure differential across the chamber body 104 between an inlet 142 and an outlet 144. The end cap 112 may comprise either the inlet 1242 or the outlet 144, and the chamber body 104 may be configured to attenuate gamma rays approximately eight times less than stainless steel, while supporting a pressure differential of at least 3 MPa between the inlet 142 and the outlet 144 when fluid 136 carrying a radioactive tag 146 to generate gamma rays as a source of energy for PET imaging flows through the hollow interior portion 114 of the chamber body 104 and the core sample 140, via the inlet 142 and the outlet 144.

In some embodiments, the apparatus 100 may be provided as a kit of parts, or assembled, including the core sample 140 and the flexible sleeve 120. In some cases, the apparatus 100 is assembled by disposing the core sample 140 within the flexible sleeve 120, and then seating the flexible sleeve 120 within the hollow interior portion 114 of the chamber body 104. Thus, the apparatus 100 may comprise the flexible sleeve 120, along with the core sample 140. In some embodiments, the chamber body 104 and the end cap 112 may comprise a thermoplastic, such as a polymer, including PEI, or a linear aromatic polymer, such as PEEK.

In contrast to conventional sample containers, the chamber body 104 is longer than the flexible sleeve 120, so that the chamber body 104 completely accommodates the entire length of the flexible sleeve 120, as well as the spacers 150, and the end plugs 152. The open ends of the chamber body 104 can thus be closed for pressurization using the end caps 112 (or one end cap 112, if the chamber body 112 is formed with one end closed), without the application of ring sleeves against protruding ends of the flexible sleeve 120, or penetration of the end caps 112 by the end plugs 152 (as occurs with conventional sample containers). Still further embodiments may be realized.

Figure 2:
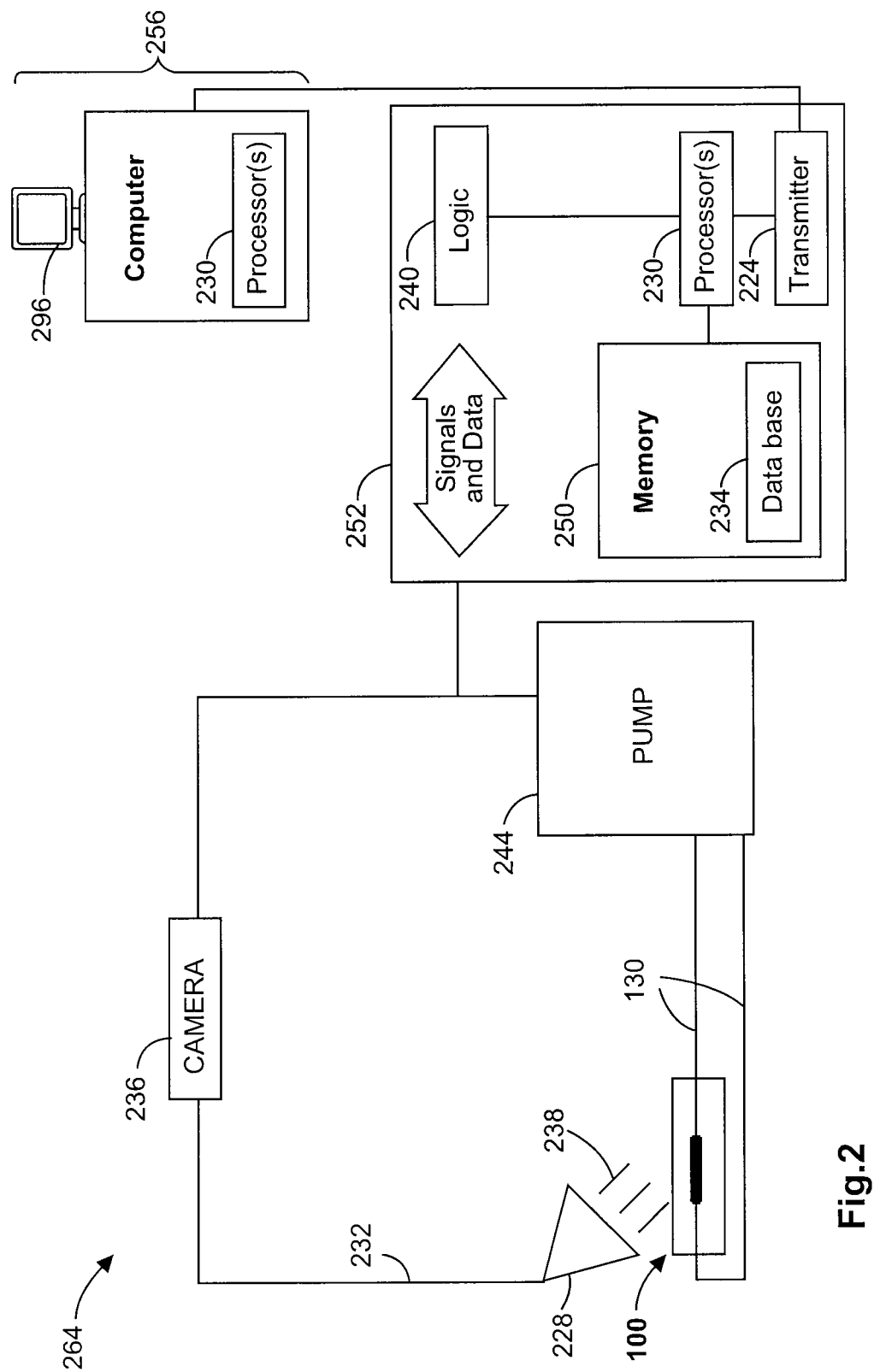
FIG. 2 illustrates system embodiments of the invention.

For example, FIG. 2 illustrates system embodiments of the invention. In some embodiments, the system 264 comprises some form of the apparatus 100 and a PET sensor 228. Thus, a system 264 may comprise a PET sensor 228 to provide a signal 232 responsive to gamma ray emissions 238. The system 264 further comprises one or more apparatus 100 configured as described previously.

Other components of the system 264 may include processors 230, memory 250, and data acquisition logic 240. The sensor 228, camera 236, pump 244, processors 230, memory 250, and logic 240 may form part of a data acquisition system 252.

The memory 250 can be used to store acquired image data, as well as other data (e.g., in a database 234). The memory 250 is communicatively coupled to the processor(s) 230.

A pump can be used to circulate fluid through the apparatus. Thus, the system 264 may further comprise a pump 244 to circulate the fluid from the outlet to the inlet of the apparatus 100, via the tubing 130.

The imaging sensor 228 may exist apart from a camera (as shown in FIG. 2), or form part of a PET camera 236. Thus, the system 264 may comprise a PET camera 236 to house the PET sensor 228, and to record the signal 232.

In some embodiments, the system 264 may comprise a display 296 to display information regarding fluid flow through the apparatus 100, as well as PET images. A transmitter 224 can be used to send data (e.g., PET image data, or signals 232) to a remote location, such as a workstation 256, perhaps for further processing/analysis. Thus, a system 264 may comprise a transmitter 224 to transmit at least a portion of the data acquired by the sensor 228 and/or the camera 236 to a remote processor 230. Thus, many embodiments may be realized.

The apparatus 100; chamber body 104; end caps 112; hollow interior portion 114; diameters 116, 118; sleeve 120; engaging ends 122; sleeve ends 126; orifices 128; tubing 130, 154; o-rings 132; end plugs 134; fluid 136; central portion 138; core sample 140; inlet 142; outlet 144; tag 146; interior portion 148; spacers 150; screen 152; transmitter 224; sensor 228; processors 230; signal 232; database 234; camera 236; emissions 238; logic 240; pump 244; memory 250; acquisition system 252; workstation 256; system 264; and display 296 may all be characterized as "modules" herein. Such modules may include hardware circuitry, and/or a processor and/or memory circuits, software program modules and objects, and/or firmware, and combinations thereof, as desired by the architect of the apparatus 100 and system 264, and as appropriate for particular implementations of various embodiments.

For example, in some embodiments, such modules may be included in an apparatus and/or system operation simulation package, such as a software electrical signal simulation package, a power usage and distribution simulation package, a power/heat dissipation simulation package, a radiation simulation and/or fluid flow package, a communications simulation package, and/or a combination of software and hardware used to simulate the operation of various potential embodiments.

It should also be understood that the apparatus and systems of various embodiments can be used in applications other than for core sample imaging operations, and thus, various embodiments are not to be so limited. The illustrations of apparatus 100 and systems 264 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as subcomponents within a variety of electronic systems, such as televisions, cellular telephones, personal computers, workstations, radios, video players, vehicles, signal processing for geothermal tools and smart transducer interface node telemetry systems, among others. Some embodiments include a number of methods.

Figure 3:
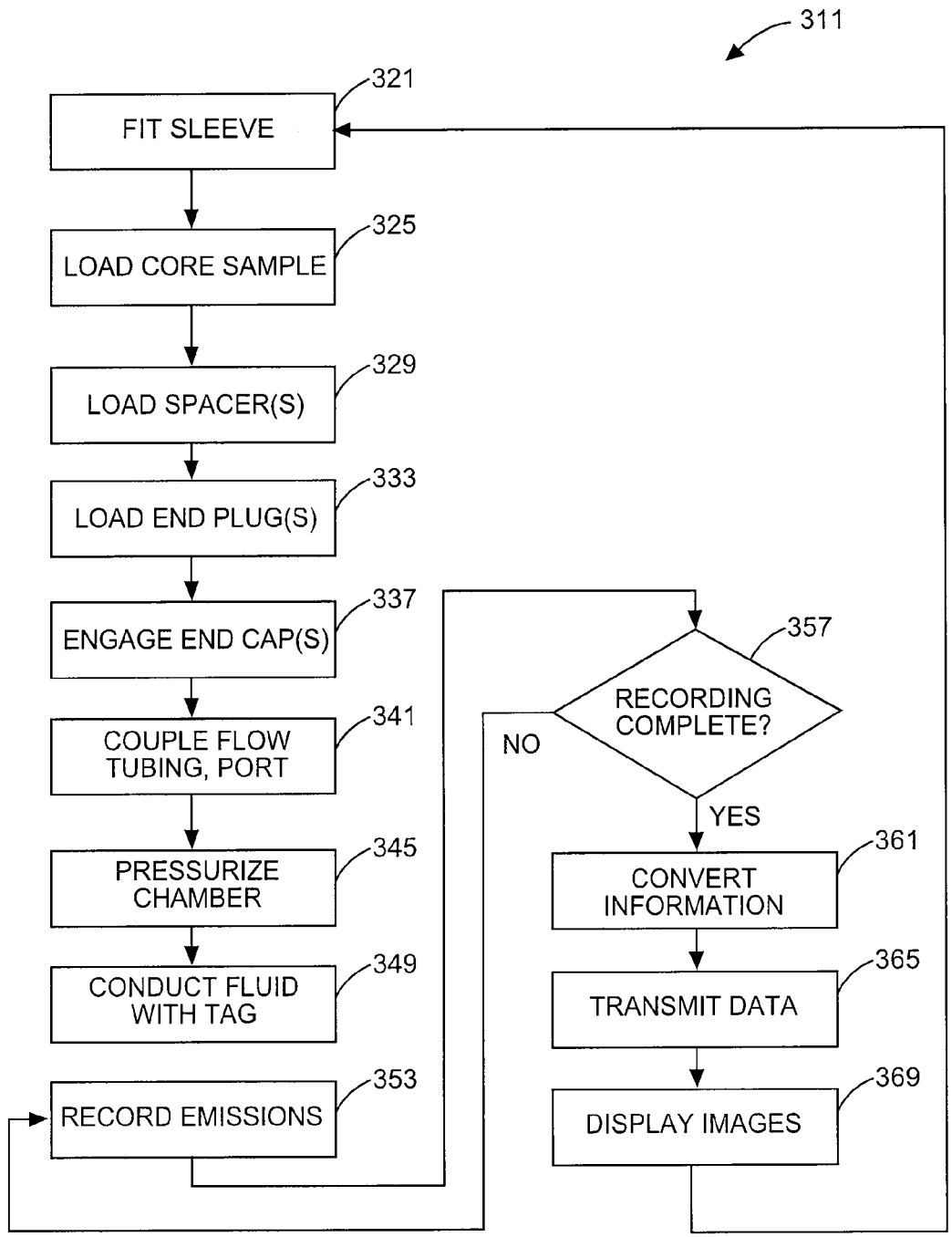
FIG. 3 is a flow chart illustrating several methods according to various embodiments of the invention.

For example, FIG. 3 is a flow chart illustrating several methods 311 according to various embodiments of the invention. The methods 311 may comprise processor-implemented methods, and may include, in some embodiments, loading a core sample into a chamber (e.g., the chamber body described previously), positioning the sample using at least end plugs (and optionally, spacers), sealing the chamber, pressurizing the chamber, forcing fluid and a tag through the chamber, and recording gamma-ray emissions.

This process can be used to determine fluid mobility in the sample. The core sample, which may comprise porous rock, can be disposed within the sleeve, and loaded into the chamber, or the sleeve can be disposed within the chamber and the core sample can be loaded into the chamber by disposing it within the sleeve. Other operational arrangements are possible.

Depending on the construction of the apparatus in use, the chamber body may have a closed end and an open end, or two open ends (as shown in FIG. 2). The following description of using the apparatus assumes that the chamber body has two open ends. If the apparatus in use has only one open end, those of ordinary skill in the art, after reading this disclosure and studying the attached figures, will understand how the method 311 can be adapted to revise the order of loading the core sample, spacers, and/or end plugs. The order of coupling to flow tubing and/or inserting flow tubing into the chamber body inlet/outlet may also be revised.

Thus, considering an apparatus with two open ends, a method 311 may begin at block 321 with fitting a flexible sleeve within a unitary chamber body, so that it is seated within and completely contained by the hollow interior portion of the chamber body. The method 311 may continue on to block 325 with loading a core sample into the chamber body, the chamber body comprising at least one engaging end and a hollow interior portion shaped to accommodate the flexible sleeve. The sleeve may be constructed so as to have a central portion attached to exterior protruding end portions, where the core sample is to be disposed within the flexible sleeve.

The method 311 may continue on to block 329 with loading spacers to center the core sample within the chamber body, between end plugs.

The method 311 may continue on to block 333 with loading at least one end plug (with an orifice) into the hollow interior portion of the chamber body, the end plug shaped to fit within an outer end of the hollow interior portion of the chamber body, as well as an interior portion of the flexible sleeve, the end plug having an orifice.

The method 311 may continue on to block 337 with coupling at least one engaging end cap having flow tubing inserted therethrough to the chamber body, the at least one engaging end cap to engage the at least one engaging end of the chamber body (in this example, two end caps engage two engaging ends of the chamber body).

The method 311 may continue on to block 341 with coupling the flow tubing to a circulation pump, and coupling the pressure port tubing to a pressurizing apparatus, such as another pump. The method 311 may continue on to block 345 with pressurizing the chamber body.

The method 311 may continue on to block 349 with conducting a fluid with a tag to the core sample, or from the core sample, via the flow tubing.

The method 311 may continue on to block 353 with recording gamma-ray emissions as recorded emission information from the tag using a PET sensor, as the tag is conducted from a first end of the chamber body to a second end of the chamber body along a longitudinal axis of the chamber body (e.g., from the inlet to the outlet of the chamber body).

At block 357, a determination is made as to whether imaging is complete. If not, the recording of emissions may continue at block 353.

If imaging is complete, as determined at block 357, the method 311 may continue on to block 361 with converting the recorded emission information into digital data. For example, the PET sensor may be included in a PET camera, to provide recorded information that can be converted into digital data.

The data derived from recording gamma-ray emissions can be sent to the surface for processing, analysis, and display. Thus, the method 311 may continue on to block 365 with transmitting the digital data to a workstation. In some embodiments, the method 311 may continue on to block 369 with displaying images derived from the digital data.

It should be noted that the methods described herein do not have to be executed in the order described, or in any particular order. Moreover, various activities described with respect to the methods identified herein can be executed in iterative, serial, or parallel fashion. The various elements of each method (e.g., the methods shown in FIG. 3) can be substituted, one for another, within and between methods. Information, including parameters, commands, operands, and other data, can be sent and received in the form of one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein. The programs may be structured in an object-orientated format using an object-oriented language such as Java or C#. Alternatively, the programs can be structured in a procedure-orientated format using a procedural language, such as assembly or C. The software components may communicate using any of a number of mechanisms well known to those skilled in the art, such as application program interfaces or inter-process communication techniques, including remote procedure calls. The teachings of various embodiments are not limited to any particular programming language or environment. Thus, other embodiments may be realized.

Figure 4:
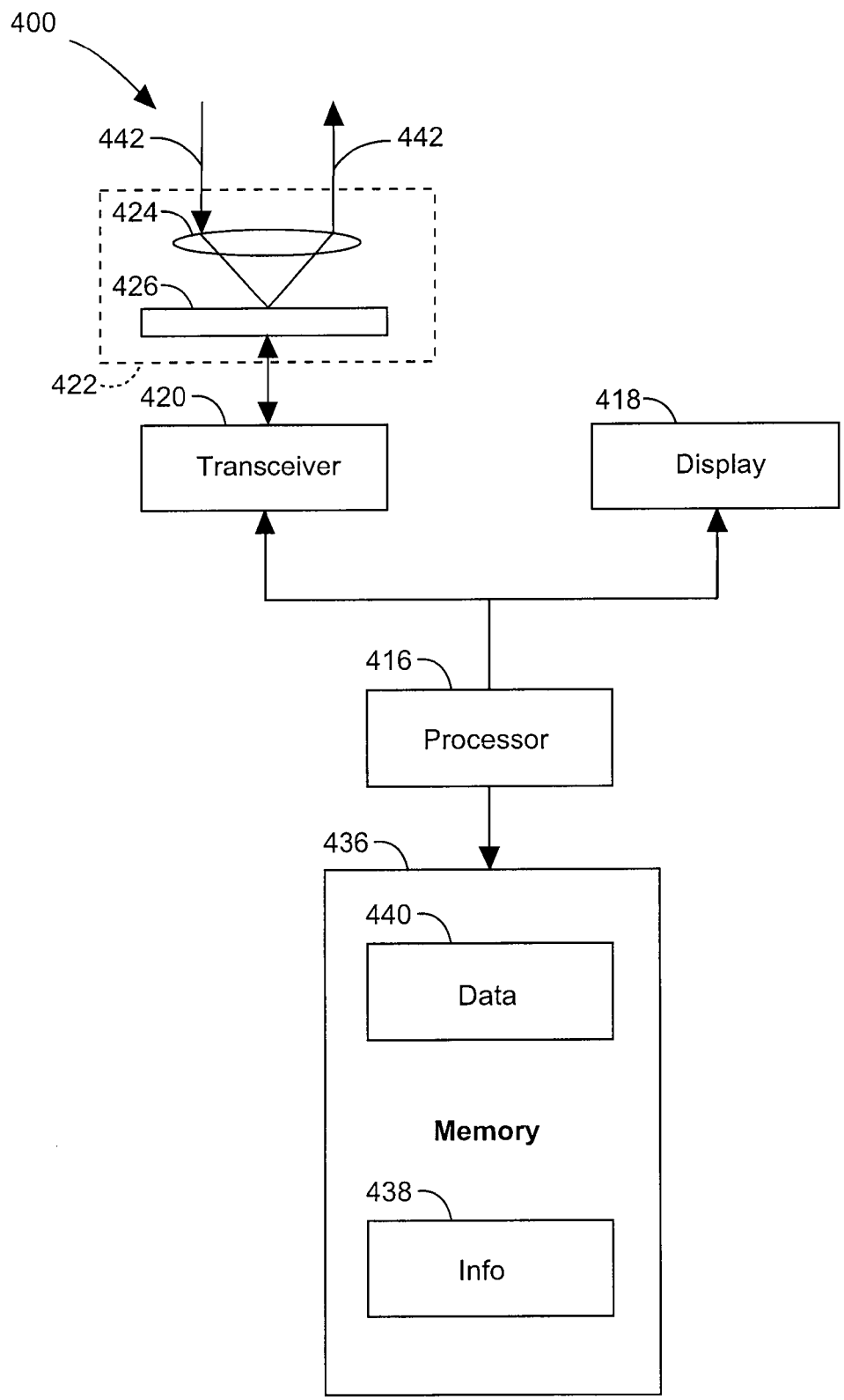
FIG. 4 is a block diagram of an article according to various embodiments of the invention.

For example, FIG. 4 is a block diagram of an article 400 according to various embodiments of the invention, such as a computer, a memory system, a magnetic or optical disk, or some other storage device. The article 400 may include one or more processors 416 coupled to a machine-accessible medium such as a memory 436 (e.g., removable storage media, as well as any tangible, non-transitory memory including an electrical, optical, or electromagnetic conductor) having associated information 438 (e.g., computer program instructions and/or data), which when executed by one or more of the processors 416, results in a machine (e.g., the article 400) performing any actions described with respect to the methods of FIG. 3, the apparatus of FIG. 1, and/or the systems of FIG. 2. The processors 416 may comprise one or more processors sold by Intel Corporation (e.g., Intel® Core™ processor family), Advanced Micro Devices (e.g., AMD Athlon™ processors), and other semiconductor manufacturers.

In some embodiments, the article 400 may comprise one or more processors 416 coupled to a display 418 to display data processed by the processor 416 and/or a wireless transceiver 420 (e.g., a local transmitter coupled to a data acquisition system) to receive and transmit data processed by the processor to another (remote) system.

The memory system(s) included in the article 400 may include memory 436 comprising volatile memory (e.g., dynamic random access memory) and/or non-volatile memory. The memory 436 may be used to store data 440 processed by the processor 416.

In various embodiments, the article 400 may comprise communication apparatus 422, which may in turn include amplifiers 426 (e.g., preamplifiers or power amplifiers) and one or more antenna 424 (e.g., transmitting antennas and/or receiving antennas). Signals 442 received or transmitted by the communication apparatus 422 may be processed according to the methods described herein.

Many variations of the article 400 are possible. For example, in various embodiments, the article 400 may comprise a data acquisition system, including the apparatus 100 shown in FIG. 1. In some embodiments, the article 400 is similar to or identical to portions of the system 264 shown in FIG. 2.

Using the apparatus, systems, and methods disclosed herein may enable PEPT and short-time (e.g. sub-second) image sampling to generate time-lapse, three-dimensional images of fluid propagation in rocks. This type of imaging is not possible using available stainless steel sample containment vessels.

In this way, imaging mobility problems of gas in small-scale (i.e. ultra-low (nD) permeability) shale rocks can be addressed, so that:

the uncertainty in quantifying the Fracture Conductivity Ratio (FCR) and the Natural Fracture Conductivity Index (NCFI) are reduced, the success of fracturing production, through the estimation of Stimulated Reservoir Volume (SRV) by imaging directionality and connectivity of fractures is determined more accurately, and fracturing and re-fracturing jobs can be optimized by improving the knowledge of the correlation of fluid propagation and fracturing attributes (e.g. closure stress), stimulation parameters (e.g. presence and type of proppants), and production data (e.g. pressure). Improved customer satisfaction may result.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, comprising:
   a unitary chamber body having a first engaging end and a hollow interior portion shaped to accommodate a flexible sleeve having a central portion attached to exterior protruding end portions, so that when the flexible sleeve is seated within the hollow interior portion of the chamber body the central portion and the end portions are entirely contained within the hollow interior portion;
   end plugs shaped to fit within outer ends of the hollow interior portion and an interior portion of the flexible sleeve such that, when the flexible sleeve is seated, the exterior protruding end portions of the flexible sleeve are arranged as a fluid-tight seal against a wall of the hollow interior portion of the unitary chamber body by the end plugs, each of the end plugs having an orifice configured to enable fluid conduction along a path substantially parallel to a longitudinal axis of the chamber body, the path including an inlet of the apparatus, each orifice, and an outlet of the apparatus;
   a port to pass through a wall of the chamber body and to couple pressure imposed external to the chamber body to the hollow interior portion when the chamber body is sealed against the pressure; and
   a first engaging end cap to engage the first engaging end of the chamber body and to provide either the inlet or the outlet.

2. The apparatus of claim 1, wherein each orifice is substantially centered in its respective end plug.

3. The apparatus of claim 1, wherein at least one of the end plugs has a length approximately equal to a distance from the first engaging end past one of the protruding end portions attached to the central portion of the flexible sleeve, when the flexible sleeve is seated within the hollow interior portion.

4. The apparatus of claim 1, wherein the chamber body forms a hollow cylinder.

5. The apparatus of claim 1, further comprising:
   a second engaging end cap to engage a second engaging end of the chamber body.

6. The apparatus of claim 1, wherein an exterior dimension of the first engaging end cap substantially matches an exterior dimension of the chamber body.

7. The apparatus of claim 1, further comprising:
   a pair of core spacers to substantially center a core sample within the hollow interior portion, between the end plugs.

8. The apparatus of claim 7, further comprising:
   a pair of screens disposed between the core spacers and the end plugs, wherein the core spacers comprise bonded sand.

9. The apparatus of claim 1, wherein the chamber body; the end plugs, and the first threaded end cap comprise a thermoplastic having sufficient tensile strength to withstand a pressure differential of more than 3 MPa between the inlet and the outlet.

10. The apparatus of claim 1, further comprising:
    port pressure compensation tubing disposed within the port.

11. The apparatus of claim 1, further comprising:
    flow tubing configured to fit within at least one of the inlet or the outlet; and
    a pair of O rings to be disposed around the flow tubing and within counter-bores in the end plugs and the hollow interior portion of the chamber body.

12. An apparatus, comprising:
    a unitary chamber body having an open end defining a hollow interior portion shaped to completely contain a flexible sleeve having a central portion attached to exterior protruding end portions, such that when the sleeve is seated within the hollow interior portion, the sleeve covers a core sample;
    end plugs shaped to fit within outer ends of the hollow interior portion and an interior portion of the flexible sleeve such that, when the flexible sleeve is seated, the exterior protruding end portions of the flexible sleeve are arranged as a fluid-tight seal against a wall of the hollow interior portion of the unitary chamber body by the end plugs;
    and at least one end cap formed to engage the open end to support a pressure differential across the chamber body between an inlet and an outlet, the end cap comprising either the inlet or the outlet, wherein the chamber body is made of polyetherimide and configured to attenuate gamma rays approximately eight times less than stainless steel, while supporting a pressure differential of at least 3 MPa between the inlet and the outlet when fluid carrying a radioactive tag to generate the gamma rays as a source of energy for positron emission tomography imaging flows through the hollow interior portion and the core sample via the inlet and the outlet.

13. The apparatus of claim 12 further comprising:
    the flexible sleeve; and
    the core sample.

14. The apparatus of claim 12, wherein the end cap comprises polyetherimide.

15. A system, comprising:
    a positron emission tomography (PET) sensor to provide a signal responsive to gamma ray emissions; and
    an apparatus comprising a unitary chamber body having an engaging end and a hollow interior portion shaped to accommodate a flexible sleeve having a central portion attached to exterior protruding end portions, so that when the flexible sleeve is seated within the hollow interior portion of the chamber body the central portion and the end portions are entirely contained within the hollow interior portion; end plugs shaped to fit within outer ends of the hollow interior portion and an interior portion of the flexible sleeve such that, when the flexible sleeve is seated, the exterior protruding end portions of the flexible sleeve are arranged as a fluid-tight seal against a wall of the hollow interior portion of the unitary chamber body by the end plugs, each of the end plugs having an orifice configured to enable fluid conduction along a path substantially parallel to a longitudinal axis of the chamber body, the path including an inlet of the apparatus, each orifice, and an outlet of the apparatus; a port to pass through a wall of the chamber body and to couple pressure imposed external to the chamber body to the hollow interior portion when the chamber body is sealed against the pressure; and an engaging end cap to engage the engaging end of the chamber body and to provide either the inlet or the outlet.

16. The system of claim 15, further comprising:
a pump to circulate the fluid from the outlet to the inlet.

17. The system of claim 15, further comprising:
a PET camera to house the PET sensor, and to record the signal.

18. A processor-implemented method to execute on one or more processors that perform the method, comprising:
loading a core sample into a unitary chamber body, the chamber body comprising at least one engaging end and a hollow interior portion shaped to accommodate a flexible sleeve having a central portion attached to exterior protruding end portions, the core sample to be disposed within the flexible sleeve;
loading at least one end plug into the hollow interior portion of the chamber body, the end plug shaped to fit within an outer end of the hollow interior portion and an interior portion of the flexible sleeve such that, when the flexible sleeve is seated, the exterior protruding end portions of the flexible sleeve are arranged as a fluid-tight seal against a wall of the hollow interior portion of the unitary chamber body by the least one end plug and another end plug arranged within an outer end of the hollow interior portion and an interior portion of the flexible sleeve opposite the at least one end plug, the end plug having an orifice;
coupling at least one engaging end cap having flow tubing inserted therethrough to the chamber body, the at least one engaging end cap to engage the at least one engaging end;
pressurizing the chamber body;
conducting a fluid with a tag to the core sample or from the core sample via the flow tubing; and
recording gamma-ray emissions as recorded emission information from the tag using a positron emission tomography (PET) sensor as the tag is conducted from a first end of the chamber body to a second end of the chamber body along a longitudinal axis of the chamber body.

19. The method of claim 18, further comprising:
converting the recorded emission information into digital data.

20. The method of claim 18, further comprising:
transmitting the digital data to a workstation, and displaying images derived from the digital data.

* * * * *

UNITED STATES PATENT AND TRADEMARK OFFICE
CERTIFICATE OF CORRECTION

| | | |
|---|---|---|
| PATENT NO. | : 8,920,029 B2 | Page 1 of 1 |
| APPLICATION NO. | : 14/000570 | |
| DATED | : December 30, 2014 | |
| INVENTOR(S) | : Maucec et al. | |

It is certified that error appears in the above-identified patent and that said Letters Patent is hereby corrected as shown below:

Claims

In column 18, line 9, in Claim 9, delete "body;" and insert --body,--, therefor

In column 18, line 10, in Claim 11, delete "O rings" and insert --O-rings--, therefor Signed and Sealed this
Tenth Day of November, 2015

Michelle K. Lee
*Director of the United States Patent and Trademark Office*